(12) United States Patent
Suzuki et al.

(10) Patent No.: US 7,001,354 B2
(45) Date of Patent: Feb. 21, 2006

(54) PERFUSION SYSTEM FOR OFF-PUMP CORONARY ARTERY BYPASS

(75) Inventors: Akira Suzuki, Nishio (JP); Masao Takahashi, Chigasaki (JP); Kazuaki Mizoguchi, 163-8, Matsushin-cho, Okayama (JP); Shigeru Nemoto, Tokyo (JP); Taro Saito, 2-21-8, Kamisuizenji, Kamisuizenji-cho, Kumamoto (JP)

(73) Assignees: Nemoto Kyorindo Co., Ltd., Tokyo (JP); Kazuaki Mizoguchi, Okayama (JP); Taro Saito, Kumamoto (JP); Go Watanabe, Ishikawa ( * ) Notice: Subject to any disclaimer, the term of this patent is extended or adjusted under 35 U.S.C. 154(b) by 36 days.

(21) Appl. No.: 10/382,633

(22) Filed: Mar. 7, 2003

(65) Prior Publication Data

US 2003/0225357 A1   Dec. 4, 2003

Related U.S. Application Data

(62) Division of application No. 09/599,730, filed on Jun. 23, 2000, now abandoned.

(30) Foreign Application Priority Data

Jun. 24, 1999 (JP) .................................. 11-178957
Jun. 21, 2000 (JP) .............................. 2000-186098

(51) Int. Cl.
*A61M 37/00* (2006.01)
*A61M 5/00* (2006.01)
*A61N 1/362* (2006.01)

(52) U.S. Cl. .................. 604/6.11; 604/6.16; 604/7; 604/9; 604/4.01; 600/17

(58) Field of Classification Search .............. 604/4.01, 604/6.06, 6.09, 6.1, 6.11, 6.16, 7–9, 65–67, 604/500, 151, 264; 422/45; 600/17–18; 623/3.1, 3.18; 210/645, 739

See application file for complete search history.

(56) References Cited

U.S. PATENT DOCUMENTS

| 3,447,479 | A | * | 6/1969 | Rosenberg | 417/271 |
|---|---|---|---|---|---|
| 4,137,913 | A | * | 2/1979 | Georgi | 604/67 |
| 4,459,977 | A | * | 7/1984 | Pizon et al. | 600/17 |
| 5,385,540 | A | * | 1/1995 | Abbott et al. | 604/6.13 |
| 5,836,925 | A | * | 11/1998 | Soltesz | 604/525 |
| 6,406,422 | B1 | * | 6/2002 | Landesberg | 600/17 |
| 6,607,698 | B1 | * | 8/2003 | Spears et al. | 422/45 |

* cited by examiner

*Primary Examiner*—Patricia Bianco
*Assistant Examiner*—Leslie R. Deak
(74) *Attorney, Agent, or Firm*—Finnegan, Henderson, Farabow, Garrett & Dunner, LLP (57) ABSTRACT

A perfusion system for off-pump coronary artery bypass is provided in order to make the off-pump coronary artery bypass easier and safer and to restrict the amount of bleeding to a degree for not affecting operations by occluding the vessel in concurrency with the perfusion, including a blood removal portion, a pump, and a perfusion portion for returning blood pumped out by the pump in the form of an injection of the blood in pulses in response to a diastolic phase of the heart.

4 Claims, 11 Drawing Sheets

PERFUSION SYSTEM FOR OFF-PUMP CORONARY ARTERY BYPASS

This is a divisional of application Ser. No. 09/599,730, filed Jun. 23, 2000, now abandoned which is incorporated herein by reference, and claims the benefit of priority under 35 U.S.C. § 120.

BACKGROUND OF THE INVENTION

1. Field of the Invention

The present invention is directed to a medical equipment which is in association with off-pump coronary artery bypass and in particular to a perfusion system for off-pump artery coronary bypass which is used for perfusion in relation to a diastolic phase of the cardiac cycle.

2. Description of the Related Art

The coronary artery is an artery which supplies blood to the myocardium and the disease or failure which results from an insufficient supply of the blood to the myocardium is referred to as ischemic heart disease.

The disturbance of blood flow in the coronary artery, one of the causes of the foregoing insufficient supply of blood, is due to formation of stenosis which results from atherosclerosis or deposition of in-blood cholesterol on the inner walls of the artery. Furthermore, such disturbance of blood flow causes a turbulent flow of blood, whereby the artery becomes subject to occlusion. The aggravation of the blood flow disturbance brings an initimal injury, which causes a blood clotting by attracting platelets, resulting in ultimately a full occlusion of the artery.

In addition, though atherosclerosis can be found anywhere in the coronary artery, in general, atherosclerosis is subject to occur at a coronary bifurcation of the artery where the shearing force of the blood flow becomes larger.

Typical examples of coronary artery disease are heart stroke (myocardial infarction) and angina.

The heart stroke occurs due to the necrosis of a portion of the myocardium when the blood to be supplied thereto is decreased or completely stopped as a result of the artery occlusion. This phenomena is medically called myocardial infarction. This is a serious symptom which occurs suddenly. This symptom is accompanied by perspiration and/or shock, and results in unconsciousness sometimes. When the heart stops completely due to heart stroke, such a phenomena is said to be cardiac arrest which leads to death.

The degree of necrosis varies depending on the amount of the affected myocardium. Due to the fact that the damaged myocardium releases a kind of enzyme into the blood, measuring the activity of such enzyme makes it possible to provide an index which indicates what degree the myocardium is damaged.

The heart stroke does not occur always due to a physical fatigue or mental fatigue or both. Unlike the case of an angina, the condition of heart stroke is not always reduced even though the patient relaxes or rests.

On the other hand, the onset of angina is due to insufficient or decreased supplies of oxygen and glucose resulting from insufficient blood supply to the myocardium as a result of the coronary artery occlusion. In such a case, the heart begins to try to generate energy through a chemical process which differs from that when sufficient blood supply is made. However, such a chemical process produces waste products which can not be excluded by a smaller amount of blood and such waste products become a cause of pain. Typically, the condition of angina appears as a tense, constricting pain at a lower portion of the breastbone or sternum. Due to the fact that such the condition is related to physical activity of the patient, taking a rest eases the pain.

Where the condition of either myocardial infarction or angina becomes worse, a coronary revascularization has to be made on the occluded or stenosed coronary artery. The coronary revascularization is divided into two types or categories: (a) intervention treatment through percutaneous transluminal coronary angioplasty (PTCA) and (b) surgical treatment through coronary artery bypass graft (CABG).

(a) Intervention treatment through percutaneous transluminal coronary angioplasty (PTCA) is a method of expanding the cross-section of the stenosed portion of the coronary artery with the usage of a balloon catheter. This method is suitable for the patient who has only one stenosed portion of the coronary artery and who can not bear a surgical operation due to a disease such as pulmonary disease in its worst condition.

(b) Surgical treatment through coronary artery bypass graft (CABG) is a surgical technique to bypass the occluded or stenosed vessel. This treatment is suitable for application on a highly stenosed or occluded coronary artery of a patient where it is impossible to perform percutaneous transluminal coronary angioplasty (PTCA) or where there are a plurality of occluded portions in the coronary artery. The details of this technique will be described hereinafter with reference to FIGS. 11(a) and 11(b).

Surgical treatment through coronary artery bypass graft (CABG) is classified into two methods: so-called 'in situ arterial grafting' and so-called 'bypass grafting'. As shown in FIG. 11(b), in general, 'bypass grafting, a bypass tube 25a using a lower extremity separated saphhenous vein graft (SVG) is anastomosed to a proximal side (aorta side) and an anastomosis 27 at a downstream side of a stenosed or occluded portion 26 of a target coronary artery 27, thereby bypassing the blood to the distal side of the coronary artery. As shown in FIG. 11(a), in 'in situ arterial grafting' which is a blood supply method by way of different passage, an appropriate arterial blood vessel such as a bypass tube 25 using an internal mammary artery (ITA) is led for anastomosis to a distal side of a coronary artery.

Because the saphenous vein graft (SVG) used in 'vein grafting' has to accommodate a venous valve, the long range graft patency is not very good, and therefore recently, employing 'in situ arterial grafting' has become the mainstream operation. In addition, some doctors employ so-called 'free arterial grafting' which is established, like so-called 'saphenous vein graft,' in such a manner that proximal and distal sides of a separated arterial vessel is anastomosed to the aorta side and the coronary artery side, respectively. In this method, though the arterial vessel is used as grafting material, due to the fact that the intimal cells of the arterial vessel after separation thereof die, the merit of this method is better than 'vein grafting' but falls far behind 'in situ arterial grafting'.

Even when such 'in situ arterial granting' is employed which is an outcome of the latest medical technology, the suture of the coronary artery having a small diameter which ranges from 1 mm to 2.5 mm inclusive has to be done in very precise fashion and the blood flow to the anastomosed portion has to be stopped. Thus, so-called 'in situ arterial grafting' is compelled to be practiced under the condition of cardiac arrest with the usage of extracorporeal circulation. The steps of such an under cardioplegic arrest bypass operation using the extracorporeal circulation are as follows:

First of all, a pre-treatment is made on the patient. While the patient is being anesthetized, the breast is opened by incising the breast along the breast bone or sternum and subsequent the same is cut. Thereafter, the pericardium which surrounds the heart is exposed. Simultaneously, an internal mammary artery is separated or a portion of a vein is extracted from the lower extremity. The patient is given heparin. Cannulas are fitted into the ascending aorta and the right atrium, respectively, and the patient is secured with a pump-oxegnator system. The blood of the patient is fed to the pump-oxegnator system for filtering. An oxygen supply device and the extracorporeal circulation provide oxygen to the patient. The aorta is clamped in order that the blood can not reach the heart. A cardioplegia solution is injected into the patient for arresting the heart. While the heart is being arrested, the blood circulation is maintained by the extracorporeal circulation. The surgeon anastomoses a vein or artery between the aorta and a distal side of the occluded or stenosed portion of the coronary artery for bypassing the occluded or stenosed portion. One or more similar bypass operations are made when there are one or more other occluded or stenosed portions of the coronary artery. Immediately upon completion of the operation and anastomosis, the breast is closed after separation of the extracorporeal circulation from the patient. The patient is transferred to a recovery room and several days are required for beginning the extubation of a tube in the trachea.

Though the foregoing under-cardioplegic arrest coronary artery bypass operation can be made without limitation of time and makes it possible to anastomose in stable fashion on the outer surface of the heart which is being made to be stationary, serious risks and problems have been pointed out. In detail, due to the fact that the coronary artery bypass operation is made under cardioplegic arrest, the aorta clamping and the extracorporeal circulation which are essential factors for the under cardioplegic arrest coronary artery bypass operation sometimes may exert a bad influence on the patient such as physical injury of the vessel, hemorrhage tendency, or insufficient supply of oxygen. For example, patheopoiesis risks of cerebral infarction, hemorrhage compliance, infection of the incision of the sternum, pneumonia, renal failure and so on can occur. Inflammatory response of the whole body of the patient raises a problem which results from the destruction of immunity and complement system of the human body when using the extracorporeal circulation. In addition, the required blood transfusion for the supplementation of the blood and blood component lost in the extracorporeal circulation sometimes becomes causes of increasing risks of AIDS and other infections.

Moreover, the extracorporeal circulation per se is very expensive to purchase and cumbersome to operate, which results in that only large scale medical institutions can use the extracorporeal circulation. In addition to this, the national interest on increasing medical care expense is being raised. Thus, developing a new technology is demanded which is capable of eliminating iatrogenic complication.

In view of such circumstances, in about 1994 in Western countries, off-pump coronary artery bypass which is made while the heart is beating was proposed and recently in Japan, off-pump coronary artery bypass has been attempted. In this off-pump coronary artery bypass, no operative wound for connecting the extracorporeal circulation is required, the patient is invaded with little medicine such as heparin when using the extracorporeal circulation, which prompts the patient's postoperative recovery. For example, conventionally, the postoperative patient is required to be kept under a strict watch for a duration of 3–7 days in the intensive care unit (ICU) and subsequently about a 1 month medical treatment in the general ward. Moreover, about 2-months of care is required before his/her rehabilitation. On the contrary, according to the newly proposed method, a medical report says that only a few days are required before leaving the hospital after the operation and one week after the operation the patient can attain his/her rehabilitation. In addition, it becomes possible to reduce the risks of blood dilution and air embolism which are inevitable when using the extracorporeal circulation. Moreover, the bleeding amount during operation can be decreased, thereby enabling the amount of blood transfusion to be reduced. Of course, the patient becomes free from pains and suffering during the training for the rehabilitation. No very expensive materials for artificial heart are required.

An example of the procedure of the foregoing off pump coronary artery bypass is as follows: While the patient is in the anesthetized condition, a target coronary artery is exposed by a median sternotomy or a 10 cm incision of the $4^{th}$ intercostal space. Thereafter, a bypass tube is prepared and at an upstream side of a portion to be anastomosed of the target coronary artery is tied or fastened with a thread. With a fixing device, only the operation field on the beating heart is fixed. Thereafter, the portion to be anastomosed of the target coronary artery is incised for the anastomosis with an internal mammary artery or a saphenous vein with the usage of a very, very thin nylon thread. When the operation and the anastomosis are completed, the tied portion is released by removing the thread therefrom and the incised portion is closed after applying a protamine to the patient. The intrachea tube is extracted from the patient such that the patient can be removed from the operation table, the patient is transferred to a recovery room, and some days later the patient is able to leave the hospital.

As described above, the foregoing off pump coronary artery bypass has become notable as an innovative approach. However, some risks and problems have been pointed out.

In the operation which is made while the heart is beating, due to the fact that the vessel of small diameter is incised on the outer surface of the heart which is being vibrated continually by the heart beating, the incision is not easy to practice. In addition, due to heavy bleeding as a result of such an incision, it becomes difficult to watch the portion to be anastomosed, which makes the anastomosis difficult to do. Moreover, tying the upstream side of the portion of the vessel to be anastomosed for the bleeding arrest causes, due to the resulting insufficient blood flow, a myocardial ischemia, which may result in a cardiac arrest. Thus, the anastomosis has to be done very quickly and very surely or precisely, which limits the use of this method. Also, this method requires an additional pre-treatment for about several minutes such as a pre-conditioning (a condition check by temporal arrest of the vessel) before the operation is initiated.

Such risks and problems can be removed by placing, like the conventional operation, experts of extracorporeal circulation and blood transfusion, thereby becoming costly.

Thus, to improve the foregoing unsatisfactory facts resulting from the myocardial ischemia, it is believed that perfusing the arterial blood to a downstream side near the portion of the coronary artery to be anastomosed is preferable. In order to realize such a perfusion, an idea has been proposed wherein one end of a tube is inserted into the femoral artery and the other end is inserted into a specific portion of the coronary artery for the purpose of perfusion using the patient's own blood flow. However, in this idea, the tube which has to be inserted into the coronary artery is required to be thin in diameter, which makes the flow restriction of the pipe higher, resulting in that the amount of blood flow becomes insufficient. U.S. Pat. No. 5,066,282 proposes a perfusion device having a blood injection pump which is out of synchronization with the heart beat. However, in the continual perfusion method which is made out of synchronization with the heart beat, the perfusion is made under compulsion and under high pressure within the closed coronary artery whose upper end is isolated. Thus, such method is non-physiologlcal and may, contrary to the purpose, cause a risky condition.

SUMMARY OF THE INVENTION

Accordingly, in order to overcome the aforementioned problems or drawbacks, the inventors conceived the present invention wherein in off-pump coronary artery bypass, when a perfusion is made in such a manner that blood removed from an arterial vessel and pumped out is returned to a specific portion of a coronary artery; the pumped-out blood is in the form of an injection of blood in pulses having a small predetermined amount of blood and such an injection is made in response to the heart beating. The inventors' further research and development arrives at the present invention which attains objects to make the off-pump coronary artery bypass easier and safer which has been said to require highly skilled technique and to restrict the bleeding amount to a degree for not affecting operations by closing the vessel in concurrency with the perfusion.

A first aspect of the present invention is to provide a perfusion system for off-pump coronary artery bypass which comprises:

blood removal means for removing blood from an arterial vessel;

pump means for pumping the resulting blood;

perfusion means for returning the blood pumped out from the pump means to a portion of a coronary artery; and a pump controller for controlling the pump means in such a manner that the pumped-out blood is in the form of an injection of blood in pulses having a small predetermined amount of blood, the injection being made in response to a diastolic phase of the heart.

A second aspect of the present invention is to provide a perfusion system according to the first aspect, wherein the controller orders the pump means to inject the blood at a predetermined speed.

A third aspect of the present invention is to provide a perfusion system according to the second aspect, wherein the predetermined small amount of the injected blood is determined in view of a target perfusion volume which depends on a blood flow obstacle portion of the coronary artery.

A fourth aspect of the present invention is to provide a perfusion system according to the third aspect, wherein the speed of the injected blood is determined on the basis of the volume amount of the injected blood and a compliance with the perfusion means.

A fifth aspect of the present invention is to provide a perfusion system according to the first aspect, wherein the perfusion means includes a catheter which is formed to be of small diameter so as to be inserted into the coronary artery, the catheter being provided with a radially enlarged portion so as to be in fluid-tight contact with an inner wall of the coronary artery, the catheter being provided with an identification color for identification in operation fields, the catheter being provided with a reinforcing member so as not to be damaged by a suture needle.

A sixth aspect of the present invention is to provide a perfusion system according to the fifth aspect, wherein the perfusion means further includes a perfusion tube which is longer, thicker, and more flexible than the catheter, the perfusion tube having a flexibility in order that the blood flown in the catheter may become similar to physiologic blood flow.

In accordance with the first aspect of the present invention, the blood is removed from the arterial vessel by the blood removal means, the resulting blood is pumped-out from the pump means, the blood pumped out from the pump means is returned to the portion of the coronary artery by the perfusion means, and the blood pumped out from the pump means is responsive to the diastolic phase of the heart, whereby the off-pump coronary artery bypass which as been said to be very difficult can be done easily.

In accordance with the second aspect of the present invention, the blood pumped out from the pump means is in the form of a pulsed fashion in the first aspect, the off-pump coronary artery bypass which becomes much easier than usual is also much safer.

In accordance with the third aspect of the present invention, in the second aspect, the pumped-out blood is of a fixed amount of volume which is determined in view of a target perfusion volume which depends on a blood flow obstacle portion of the coronary artery, by which adjusting the amount of perfused blood makes the off pump coronary artery bypass much safer.

In accordance with the fourth aspect of the present invention, in the third aspect, the fixed rate of the pumped-out blood is determined on the basis of the volume amount of the pumped-out blood and a compliance of the perfusion means, by which the amount of the perfused blood is optimized and the off pump coronary artery bypass becomes much safer.

In accordance with the fifth aspect of the present invention, in the first aspect, the perfusion means includes a catheter which is formed to be of small diameter so as to be inserted into the coronary artery, the catheter being provided with a radially enlarged portion so as to be in fluid-tight contact with an inner wall of the coronary artery, the catheter being provided with an identification color for identification in operation fields, the catheter being provided with a reinforcing member so as not to be damaged by a suture needle. Thus, a local occlusion of the vessel becomes possible in concurrency with the perfusion, an easy, safety insertion of the catheter into the coronary artery can be ensured.

In accordance with the sixth aspect of the present invention, in the fifth aspect, the perfusion means further includes a perfusion tube which is longer, thicker, and more flexible than the catheter, the perfusion tube having a flexibility in order that the blood flown in the catheter may become similar to physiologic blood flow. Thus, it becomes possible to approximate the patient's own perfused blood to the physiologic blood flow.

BRIEF DESCRIPTION OF THE DRAWINGS

The above and other objects, features and advantages of the present invention will be more apparent and more readily appreciated from the following detailed description of preferred exemplary embodiments of the present invention, taken in connection with the accompanying drawings, in which.

DETAILED DESCRIPTION OF THE PRESENT INVENTION

A preferred embodiment of the present invention will be described hereinafter in detail with reference to the accompanying drawings.

Figure 1:
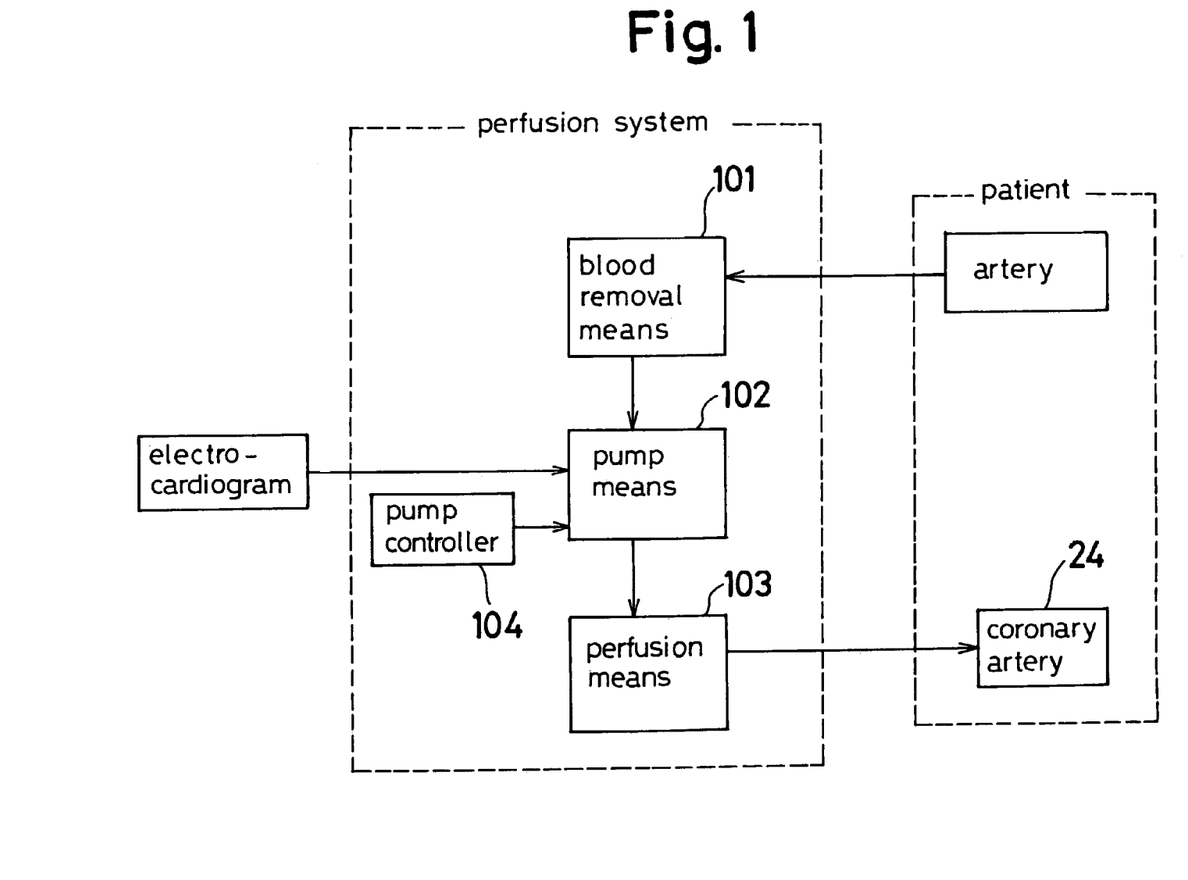
FIG. 1 illustrates a block diagram of a perfusion system for off-pump coronary artery bypass in accordance with an embodiment of the present invention.

First of all, with reference to FIG. 1, there is illustrated schematically a perfusion system for off-pump coronary artery bypass. The perfusion system includes a blood removal means 101 which is used for removing blood from a specific artery vessel of a patient (FIG. 2), a pump means 102 which injects the resulting blood, a perfusion means 103 which returns the pumped-out blood from the pump means 102 to a portion of a coronary artery, and a pump controller 104 which controls the pump means 102 in such a manner that the pump means 102 injects, in a pulsed fashion, a very small predetermined amount of the blood which comes from the blood removal means 101 at fixed rates in volume and speed during the diastolic phase of the cardiac cycle.

Figure 2:
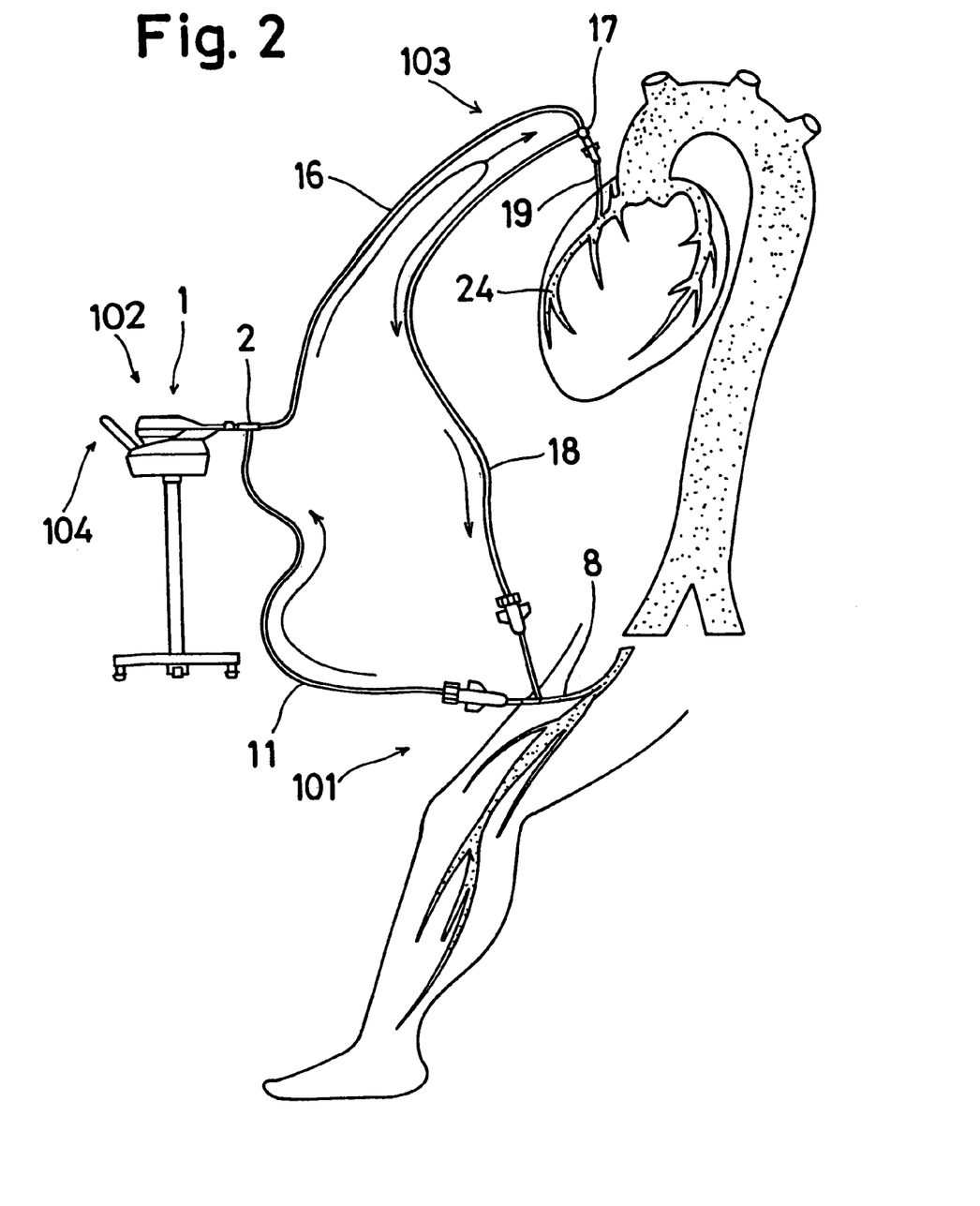
FIG. 2 illustrates an over view of how the perfusion system shown in FIG. 1 is used.

As shown in FIG. 2, in the perfusion system according to one embodiment of the present invention, the blood removal means 101 for removing blood from the arterial vessel has a catheter 8 for the purpose of blood removal and a flexible tube 11. The pump means 102 which injects the blood which comes from the blood removal means 101 is in the form of a syringe pump 1 which operates in reciprocal fashion in response to the heart beat. The perfusion means 103 has a blood transmission tube 16 and a perfusion catheter 19. The pump controller 104 controls the pump means 102 in such a manner that the pump means 102 injects, in a pulsed fashion, a very small amount of the blood which comes from the blood removal means 101 at a predetermined rate during the diastolic phase of the cardiac cycle, on the basis of an electrocardiograph signal which comes directly or by way of an ECG (not shown) from a skin or an epicardial of the patient.

The perfusion system according to one embodiment of the present invention establishes a perfusion of the patient's own arterial blood from the perfusion means 103 to a portion in the coronary artery which is at a downstream of a bypassed anastomois portion during the diastolic phase of the cardiac cycle in such manner that a cooperation of the pump means 102 which is in the form of the syringe pump 1 and a passage switching valve 2 removes the arterial blood from the patient's blood vessel by way of the blood removal means 101 having the catheter 8 and the tube 11. The pump means 102 injects the blood to the perfusion means 103 on the basis of the electrocardiogram signal which comes directly or by way of the heartbeat monitoring device (not shown) from the skim or the epicardial of the patient.

A blood return tube 18 is connected at one end to the perfusion means 103 by way of a three-way valve 17. The other end of the blood return tube 18 is connected to the blood removal catheter 8. When the perfusion is made, the three-way valve 17 makes the blood transmission tube 16 connect to and disconnect from the perfusion catheter 19 and the blood return tube 18, respectively. On the other hand, upon blood return, the three-way valve 17 makes the tube 16 disconnect from and connect to the catheter 19 and the tube 18, respectively.

In the present embodiment, the pump means 102 which is in the form of syringe pump 1 is designed to inject or pump out a predetermined amount of blood in a pulsed fashion or in a pulsating current mode in response to the heart beat under heart beating similar to natural blood flow though the coronary artery. Therefore, the pump controller 104 for controlling the pump means 102 is requested to establish automatic controls of the cycle, volume, and speed of the blood in pulses to be injected from the pump means 102 on the basis of heart beat information fed from the external monitoring device such as the electrocardiogram.

The pump controller 104 includes a means for transmitting the cycle and volume of the blood which are calculated based on a previously set mean flow when an extreme bradycardia or cardiac arrest occur.

Though any type pump is available so long as the foregoing objects can be achieved, the inventor's research found that a pump having a minutiae syringe of reciprocation driving type and a flow passage switching valve is preferred due to the fact that such a pump is able to inject blood flow which is substantially close to that of the heart and to establish a precise flow rate control of the blood. That is to say, as will be detailed later, a minute or very small amount of blood injection is required in order to establish a perfusion by a quasi-physiological pulse flow whose required maximum amount of 50 ml per minute is realized at an injection frequency of 120 times per minute even when an elongated thin tube is used as the perfusion means. The pump with a minutiae syringe can meet such a request easily, resulting in that in this respect the syringe type minutiae pump is concluded to be preferable.

Figure 4:
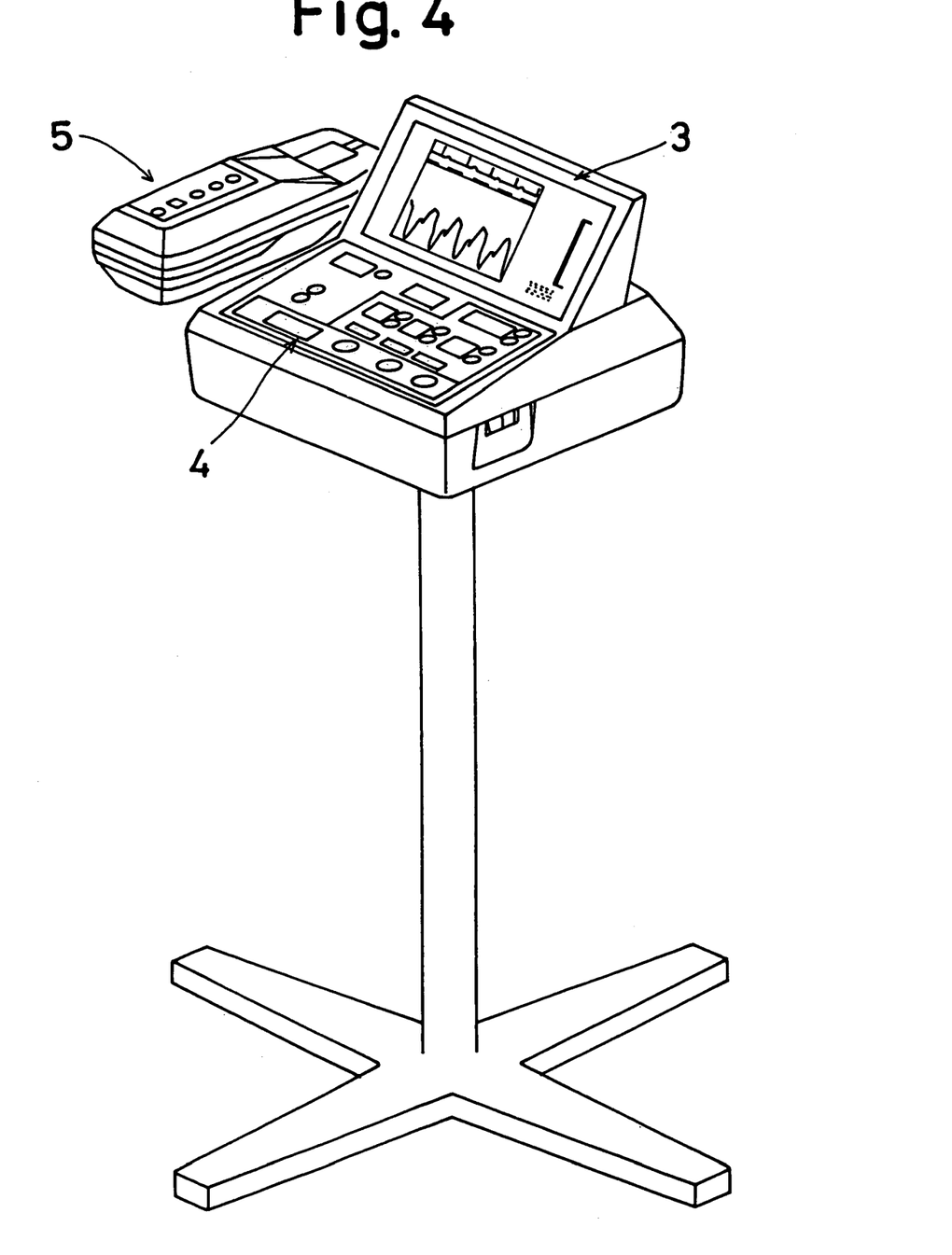
FIG. 4 illustrates a perspective view of the perfusion system shown in FIG. 1.

Referring now to FIG. 4, there is illustrated a perspective view of the pump controller 104 having a casing in which the pump means 102 is accommodated or concealed. The pump controller 104 has a heart beat related portion 3 with a liquid-crystal screen on which heart beat data from the patient such as electrocardiogram and pressure wave-form are displayed continually. Such data are used to define the instant of injection. The displaying function to visualize the heart beat data is preferable for the conformations of the blood injection and the heart beat timing. However, this function is not essential.

The pump controller 104 also includes an injection operation portion 4 which differentiates or adjusts the amount of the blood to be injected from the pump means 102 depending on different lesioned portions of coronary artery. The amounts of blood to be injected are previously set and stored as set values. The set values determine respective axial displacements and speeds of the piston 13 (FIG. 6) and the heart beat data determine the timing of reciprocation of the piston 13.

Figure 5:
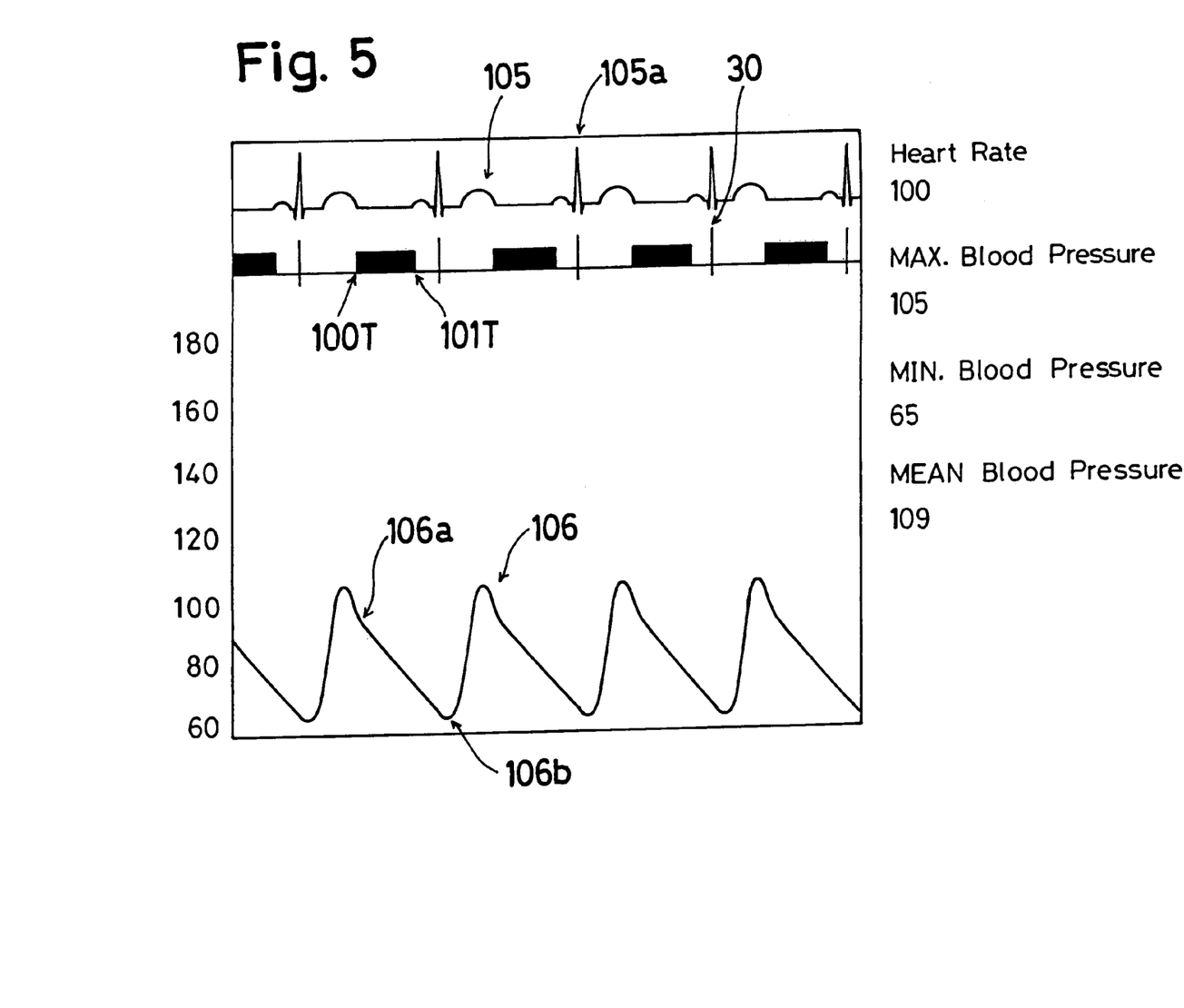
FIG. 5 illustrates an example of on-screen condition of the perfusion system.

In FIG. 5, there is illustrated an enlarged scale of the on-screen condition of the heart beat related portion 3 shown in FIG. 4. The screen displays an electrocardiogram waveform 105 and a blood pressure waveform 106 continually with the passing of time. A trigger mark 30 is plotted or marked on the screen whenever an R-event of the electrocardiogram occurs. An injection initiation timing mark 100T and an injection termination mark 101T are marked on the screen whenever the blood injection through the perfusion catheter 19 is initiated and terminated, respectively.

A delay time duration is previously prepared which occurs between an appearance of the trigger mark 30 every time the heart beats and urges the piston to stroke in the direction of blood injection by manipulating a dial switch (not shown). Whenever the delay time duration elapses, the syringe pump 1 is initiated to be driven to inject the blood. Due to the fact that the blood transmission tube 18 is flexible, a time lag is inevitable from such an initiation of the syringe pump 1 to the initiation of the blood injection through the perfusion catheter 19. Thus, the appearance, of the heart beat timing mark 100T is set in consideration of the summation of such time delay duration and time lag. Likewise, the appearance of the injection termination mark 101T is set by taking consideration of a time lag between stopping the syringe pump 1 and a termination of blood in the perfusion catheter 19.

A time duration during which the syringe pump 1 moves for injecting the blood is determined automatically by a stroke volume and a piston speed. Though the blood pressure waveform 106 per se is generally available, a systole beginning 106b and a diastole beginning 106a appear thereon, which makes it possible to watch visually and easily the diastolic phase of a cardiac cycle. Adjusting the time delay duration can be made easily on the basis of the blood pressure waveform 106 in such a manner that the heart beat initiation mark 100T and the injection termination mark 101T are made to fall within the diastolic phase of the cardiac cycle. Thus, displaying the heart beat data and timing makes it possible to confirm the correctness of the synchronization in visual fashion and to establish a fine adjustment of timing, which makes such a display preferable.

The appearance of the heart beat timing mark 101T can be omitted for making the display more simple due to the fact that when the mark 101T appears the pressure in the tube 16 is being decreased and an overlap of the termination of the heart beat and the duration of the systole falls to raise a serious problem. It is to be noted that when there is an extremely bradycardia or an cardiac arrest, the frequency of the appearance of the injection initiation mark 100T can be adjusted manually to a fixed timing value of, for example, 80 times per minute. The reverse movement of the syringe pump 1 is designed to initiate immediately upon or after termination of the blood injection movement.

Figure 6:
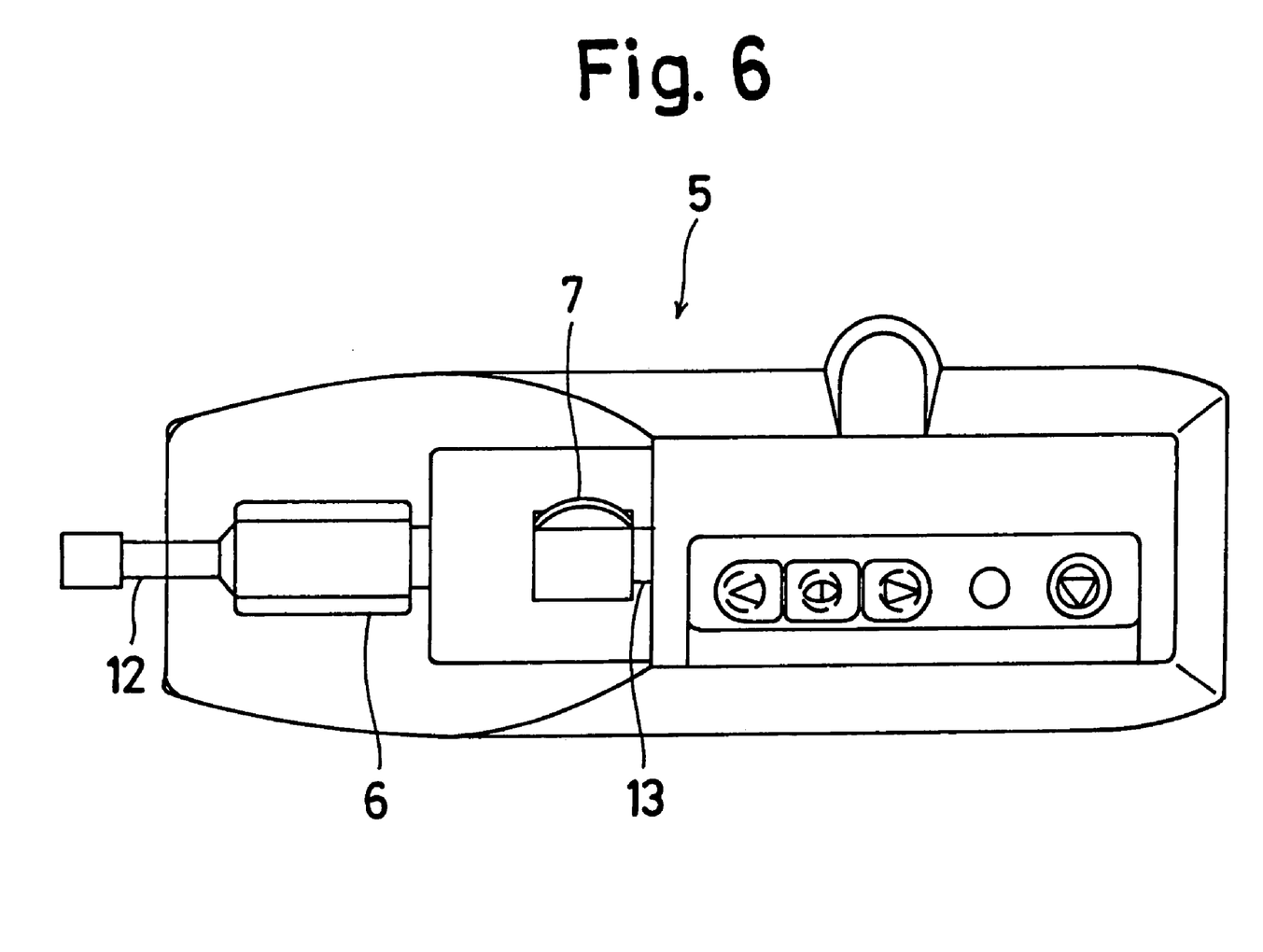
FIG. 6 illustrates a top view of an injection portion of the perfusion system.

The injecting portion 5 of the pump controller 104 which is shown in FIG. 4 includes, as illustrated in FIG. 6, a syringe holder 6 holding a syringe 12 and a piston holder 7 holding the piston 13. The injecting portion 5 has an electric motor (not shown) which moves the piston 13 in frontward and rearward directions. If the piston 13 is moved in the rearward direction and the frontward direction the blood is sucked and discharged, respectively.

The piston 13 is designed to operate such that its frontward and rearward movements are the same in stroke, which provides equal blood intake and discharging amounts. The amounts are set to be approximately 0.05–0.5 ml per stroke. The piston 13 strokes to discharge the blood during the diastolic phase of the cardiac cycle in synchronization with the heart beat which varies normally from 50 to 120 times per minute and to intake the blood during other than the diastolic phase.

Figure 7:
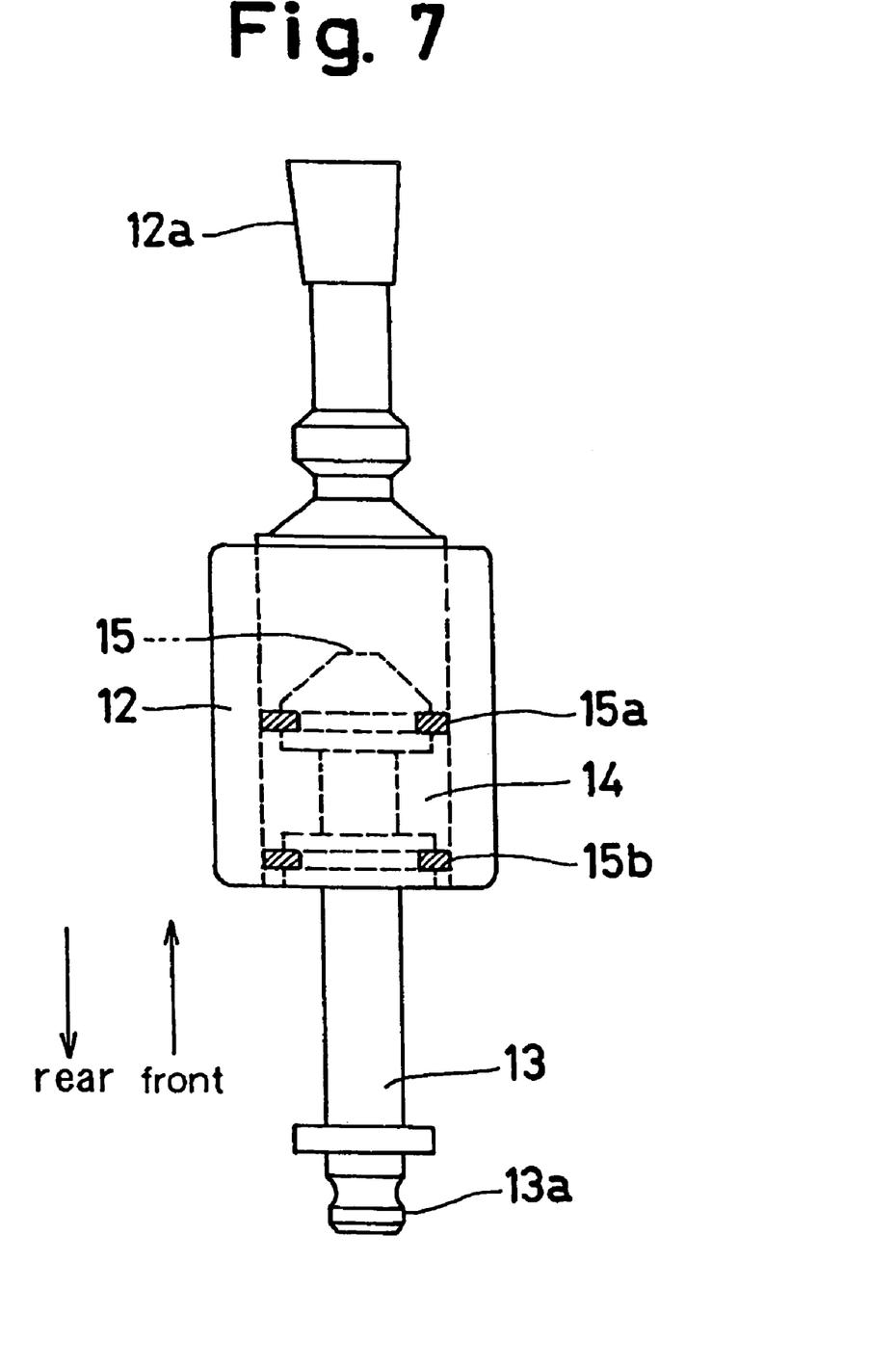
FIG. 7 illustrates a cross-sectional view of a syringe as an element of the injection portion shown in FIG. 6.

In the present embodiment, the syringe 12 is of a preferable miniaturized structure having an inner diameter of 16 mm, a cross-sectional area of 2 cm. sup. 2, and a volume of 5 ml. Preferably, the piston 13 has a hardened piston head 15 as shown in FIG. 7 for establishing the fixed amount blood injection under high pressure which is made by reciprocating the piston 13 with high frequency. In addition, the syringe 12 preferably has at a distal end portion thereof a rod connector 12a to be connected to a valve 2 as will be detailed later.

Preferably, the piston 13 of syringe 12, as shown in FIG. 7, has a pair of axially spaced sealing members 15a and 15b. If the stroke of the piston 13 is set to be less than or equal to a span between the sealing members 15a and 15b, an inner wall of the syringe which is to be in contact with the blood fails to be in contact with ambient air even though the piston 13 takes its full frontward position and remains within a clean space 14 defined between the sealing members 15a and 15b. Thus, the blood intake and discharging can be made without fear or risk of airborne infection. The piston 13 preferably has at a proximate portion thereof a lock connector 13a and related parts for an easy connection with the piston holder 7.

Figure 8:
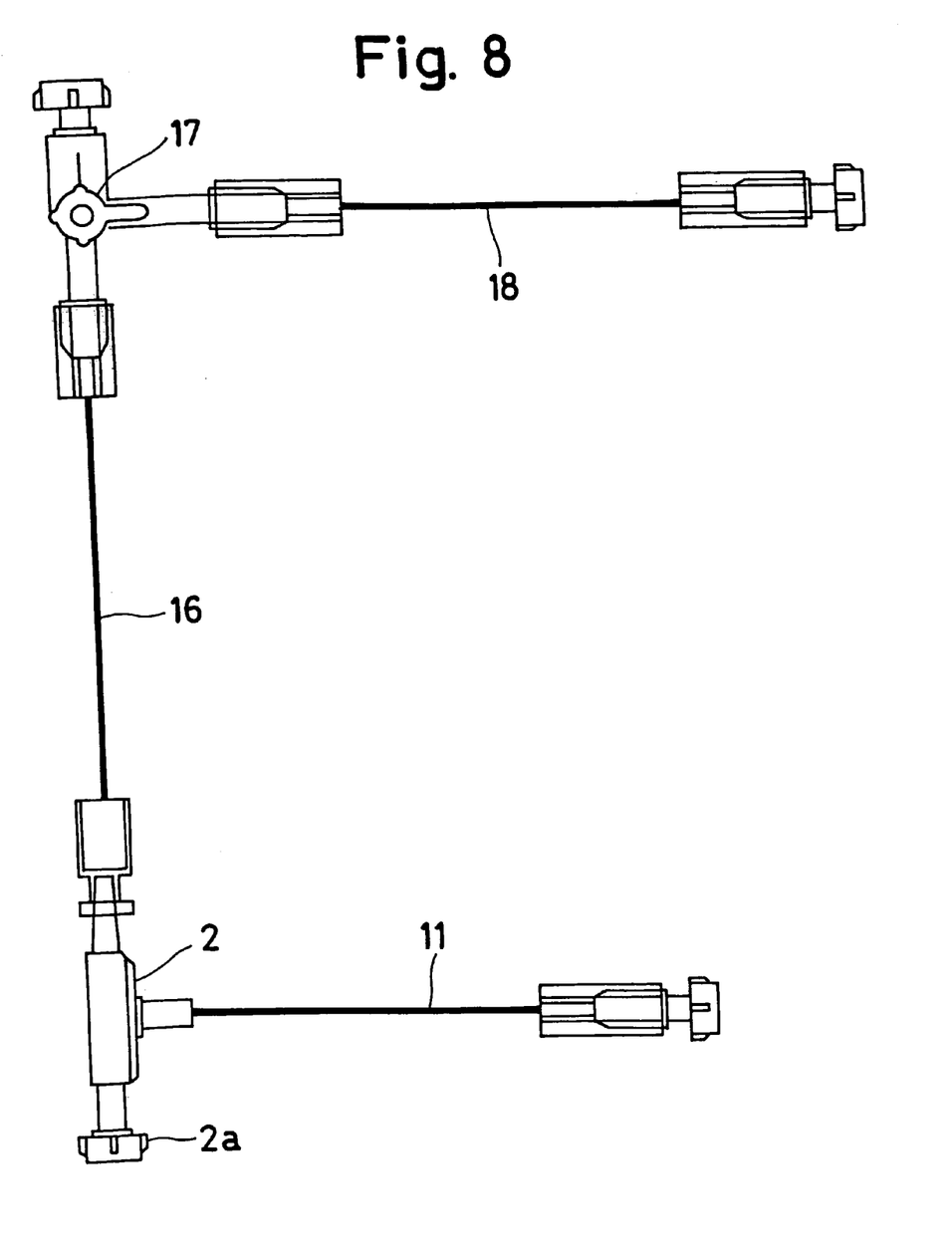
FIG. 8 illustrates a passage switching valve coupled to a blood transmission means.

Referring to FIG. 8, the passage switching valve 2 has three ports: a first port, a second port, and a third port which are connected to the lock connector 2a of the syringe, the arterial blood removing tube 11, and the blood transmission tube 16, respectively. In the second port of the valve 2, there is provided a one-way valve (not shown) which permits flowing the blood from the blood removing tube 11. In the third port, there is provided a one-way valve (not shown) which permits blood flow to the tube 16.

Thus, when the piston 13 is retracted or moved in the rearward direction, the resulting negative pressure in the syringe 12 causes the one-way valves of the sides of the tube 11 and the tube 16 to open and close, respectively, resulting in the blood being sucked into the syringe 12. Subsequent to this, when the piston 13 is moved in the frontward direction, the resultant positive pressure causes the one-way valves of the sides of the tube 11 and the tube 16 to close and open, respectively. Preferably, such one-way valves operate depending on positive and negative pressures and do not require external driving forces.

The perfusion means 103 is made up of the perfusion catheter 19 and the blood transmission tube 16. The perfusion catheter 19 is formed of a flexible and elastic shaft-like pipe or tube having an outer diameter of 0.8 mm and a length of 30 cm. The catheter 19 is capable of being inserted into the coronary artery with an inner diameter of approximately 1 mm for perfusion. The tube 18 is formed of a material having a Shore hardness of about 83A, an outer diameter of about 4 mm, an inner diameter of about 3 mm, and a length of about 150 cm.

Figure 9:
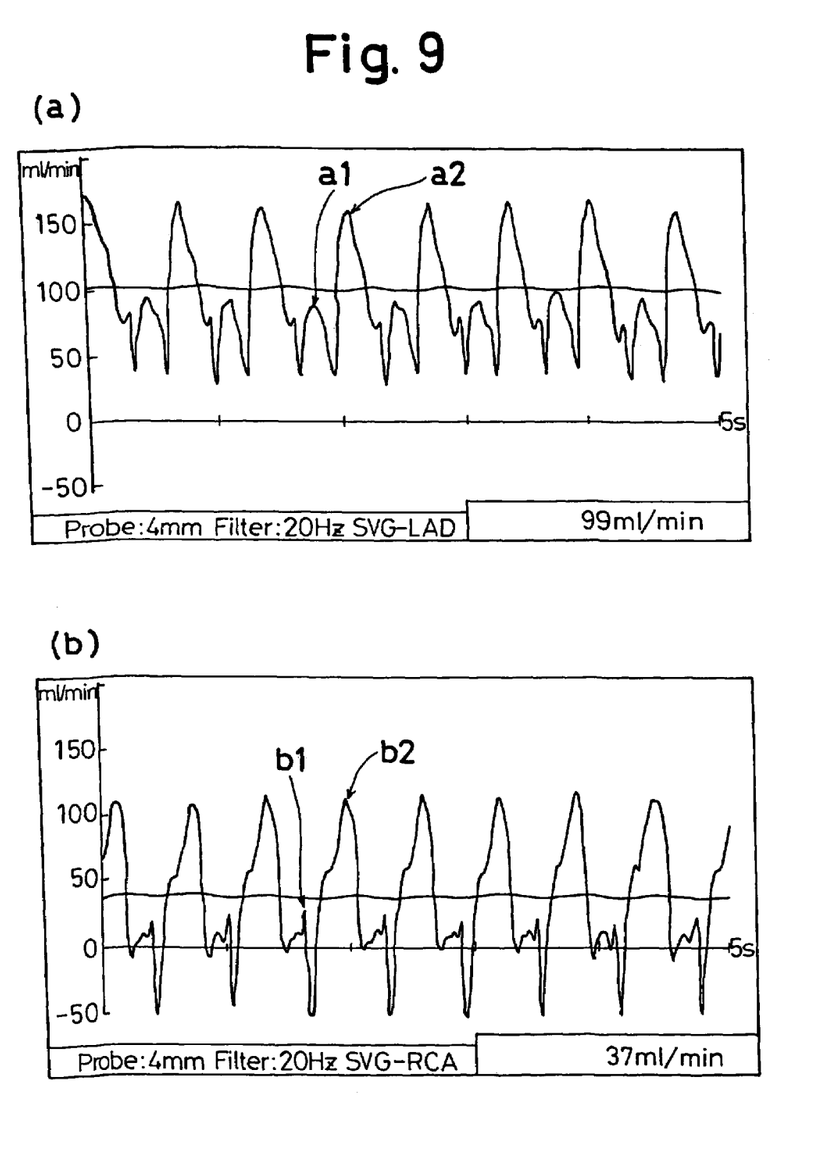
FIGS. 9(a) and 9(b) illustrate a waveform, of blood injected by the perfusion system and a waveform of physiologic blood flow, respectively.

Thus, even if a very small amount which ranges from 0.05 to 0.5 ml of blood is injected under a high pressure of 70 PSI in an instant of about 0.2 seconds, the resulting flow of blood remains the quasi-physiologic blood flow as apparent from the correlation between FIGS. 9(a) and 9(b) and the delayed time duration which ranges from the initiation of the stroke of the piston to the beginning of the vomiting of blood is restricted to about 200 mil-seconds.

In order to obtain the physiologic blood flow, the injecting speed of not less than 0.5 ml per second is found to be suitable if 0.1 ml blood is injected when the cardiac rate is 60, while the injecting speed of not less than 3.9 ml per second is found to be suitable if 0.4 ml blood is injected when the cardiac rate is 120.

FIG. 9(a) indicates a graph of the waveform of the blood flow between a left anterior descending artery (LAD) and an aorta (AO) when using SVG which is obtained by an ultra sound flow meter (not shown) utilizing the Doppler effect. This graph shows that a blood flow amount waveform a1 during the systole is smaller when compared with a blood flow amount waveform a2 during the diastole, which results in that the amount of blood flow is found to be restricted by the expansion and shrinkage of the cardiac muscle. FIG. 9(b) indicates a graph of the blood waveform which flows through the SVG anastomosed with a right coronary artery (RCA) when the SVG is connected with the perfusion system according to the present invention. In comparison with the flow amount waveform b2 during the diastole, the blood flow amount waveform b1 during the systole is found to be smaller, which indicates that the graph (b) is similar to the graph (a) in shape. That is to say, the graph (b) indicates a during-diastole superior waveform which is said to be physiological as bypassed blood.

Figure 10:
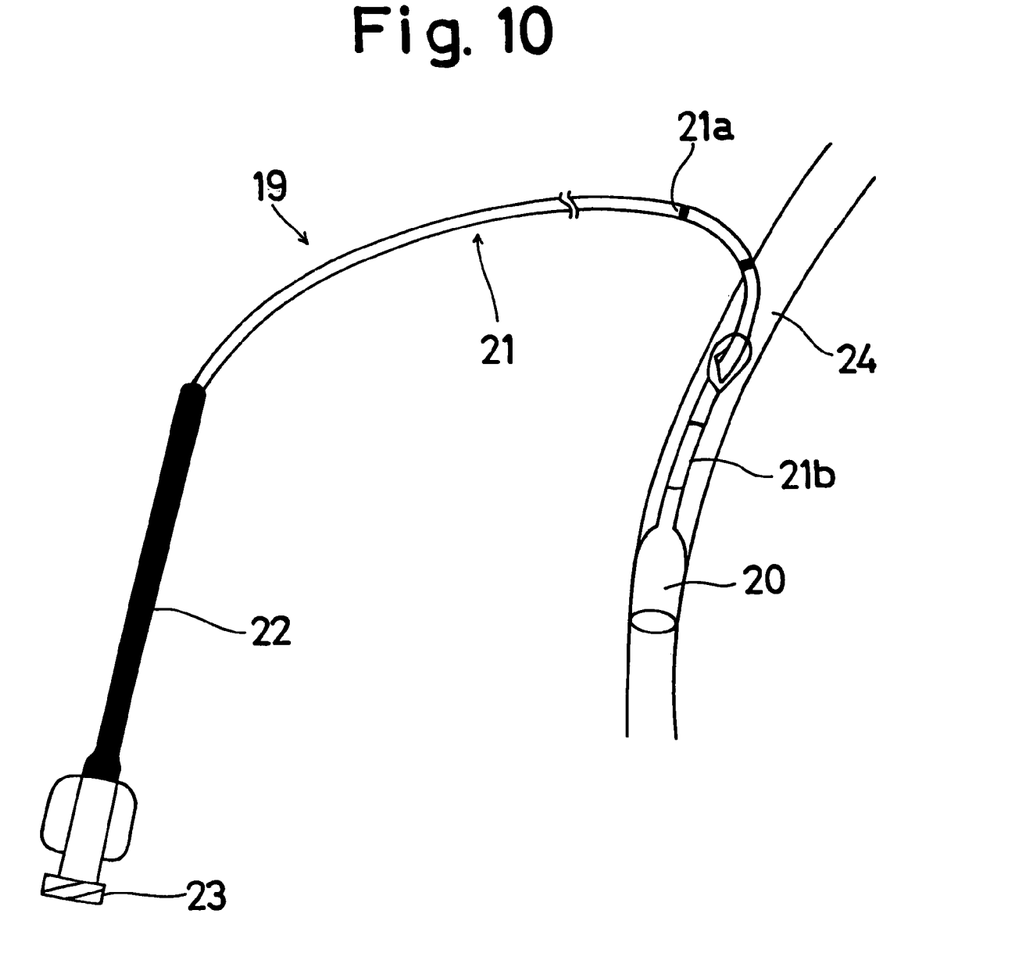
FIG. 10 illustrates a perfusion catheter when in use.

Referring to FIG. 10, there is illustrated the perfusion catheter 19 when it is inserted into the coronary artery. The perfusion catheter 19 includes, in addition to a shaft 21 having an outer diameter of 0.8 mm, an enlarged fixing portion 20 having an outer diameter larger than that of the shaft 21 and secured to a distal end thereof. The enlarged fixing portion 20 is designed to be brought into contact with an inner wall of the coronary artery when inserted therein. Employing such a fixing portion 20 which is slightly larger than an inner diameter of the artery makes it possible to establish a stable condition of the catheter while being inserted into the coronary artery and serves to prevent counterflow of the blood.

The identification markers 21a which are marked at an interval of 1 cm make it possible to determine the insertion degree of the perfusion catheter 19 easily. Coloring the shaft 21 at 21b with white allows easy viewing of the catheter shaft 21 when used in an operation field to view it being turned to red with the blood. A manually handling portion 22 of the catheter 21 is preferable to be made thereon with a knurl portion similar to a file. The manually handling portion 22 includes at its end portion a lock connector 23 to be connected with the blood transfer tube 18.

Thus, the outer diameter of the enlarged fixing portion 20 can be set depending on the diameter of a portion of the vessel in which the perfusion catheter 19 is inserted. As standard examples, the outer diameter of the enlarged fixing portion 20 is selected from one of 1.25, 1.5, 1.75, 2.0, and 2.5 mm. It is preferable that the enlarged fixing portion 20 changes in diameter like an ellipse. Coinciding the outer diameter of the shaft 21 with the inner diameter of the vessel makes it possible to establish a perfusion at a rate of about 300 ml per minute. However, setting the outer diameter of the shaft 21 to be 0.8 mm establishes perfusion at a maximum rate of 50 ml per minute and seldom creates problems in practice.

About 5 cm extension of the distal end portion of the perfusion catheter 19 is fitted therein with a metal-made reinforcing member 25 which is in the form of a spiral coil formed of thin wire. Of course, instead of such a spiral coil, a meshed metal-member is available. In addition, the reinforcing member 25 can be placed outside the perfusion catheter 19 or embedded within the wall of the perfusion catheter 19.

With the foregoing perfusion catheter 19, concurrent local closure and perfusion become possible at a more than 1 mm outer diameter distal end of an incised part of the coronary artery, which ensures a focus or local operation can be established in such a manner that the prevention of counterflow of blood and no blood in the field are assured while the perfusion is being maintained for the prevention of the myocardial ischemia at the coronary artery or its distal end.

Figure 3:
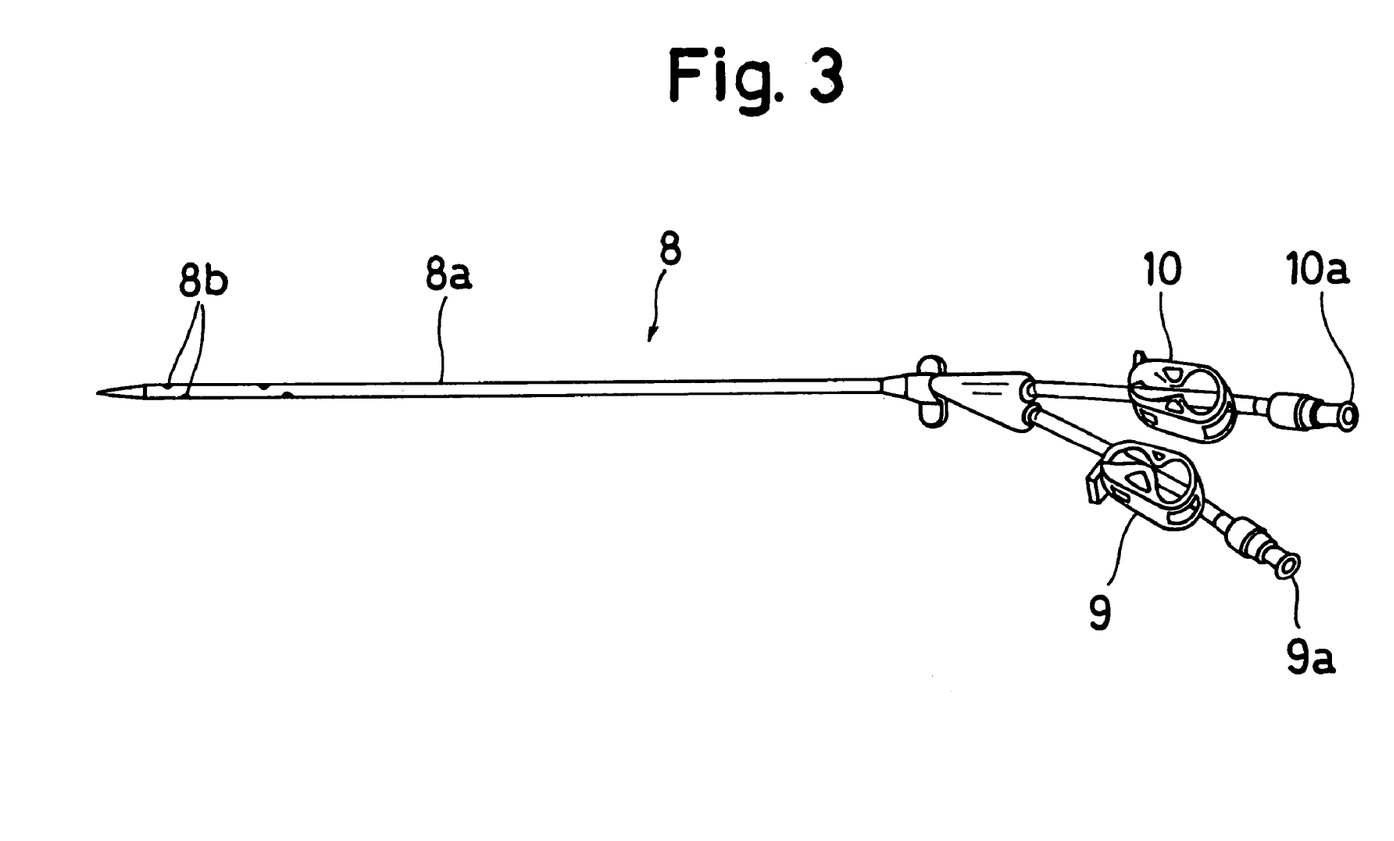
FIG. 3 illustrates a perspective view of a catheter for blood removal.

Referring to FIG. 3, there is illustrated the blood removal catheter 8 which includes a coaxial double lumen type catheter shaft 8a with an outer diameter of 2.3 mm. A distal end of the catheter shaft 8a is opened and is in fluid communication with a locking connector 10a by way of an inner passage in the catheter shaft 8a. When the catheter 8 is in use, the connector 10a is coupled to the blood return tube 18. A plurality of side holes 8b are provided in the vicinity of a proximal end of the catheter shaft 8a and are in fluid communication with a locking connector 9a by way of an outer passage in the catheter shaft 8a. When the catheter 8 is in use, the locking connector 9a is coupled to the blood removal tube 11.

Figure 11:
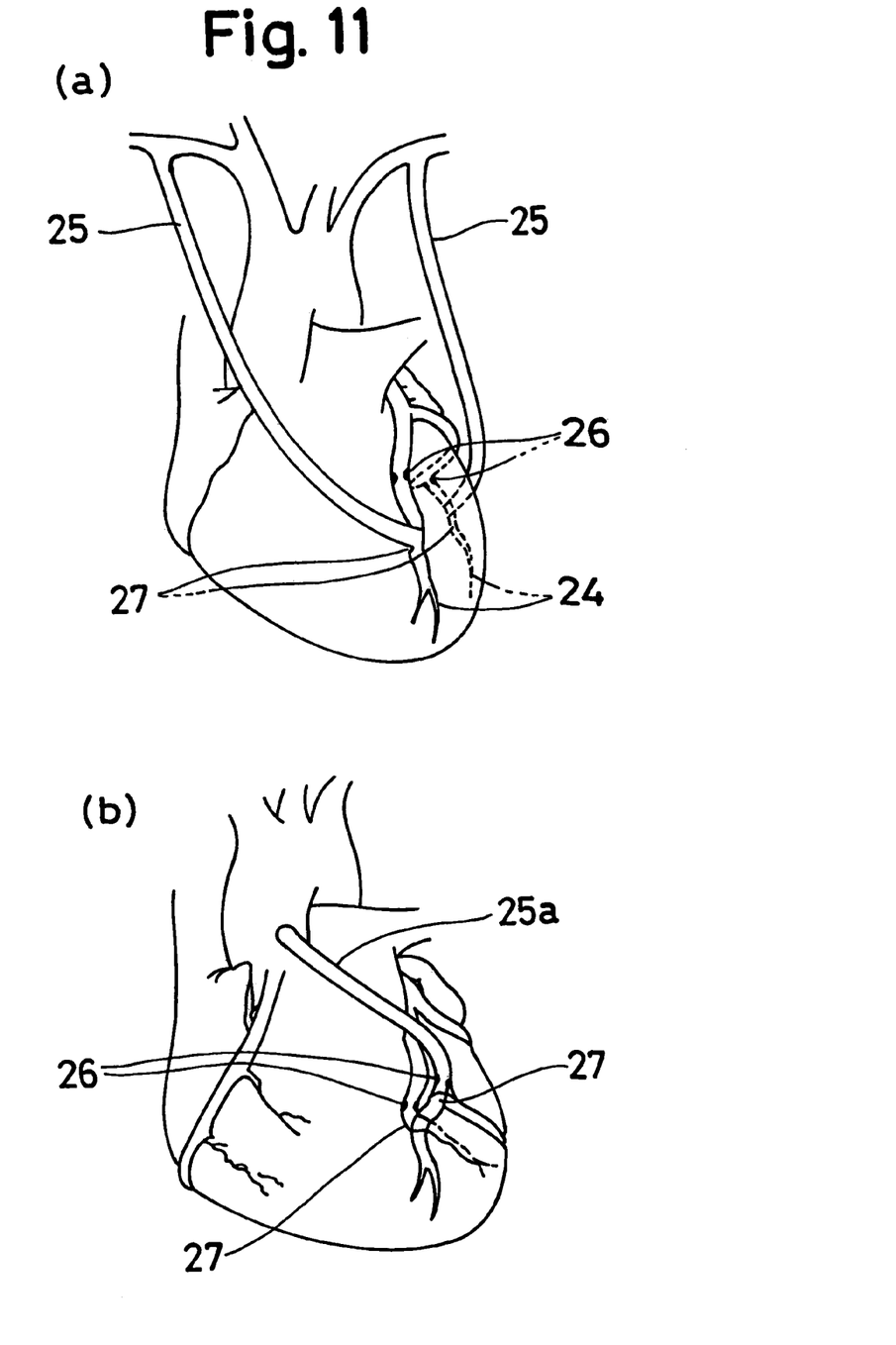
FIGS. 11(a) and 11(b) illustrate respective examples of off-pump coronary artery bypass.

As shown in FIG. 11, the perfusion system of the present embodiment is applied to off-pump coronary artery bypass, which provides an effect that an arterial blood can be fed, in synchronization with the heart beat, to a portion of the coronary artery which is on the downstream side of the anastomosed portion of the bypass tube.

In FIGS. 11(a) and 11(b), reference codes 24, 25, 25a, 26, and 27 denote a target coronary artery, an ITA bypass tube, an SVG bypass tube, a stenosed or occluded portion, and an anastomosis, respectively.

In the present embodiment, feeding the arterial blood is possible in synchronization with the heart beat while maintaining the stopping of bleeding, which makes it possible to establish prevention of shock resulting from a temporal interruption of the blood, whereby the expert becomes free from the time limit upon sutura.

In addition, the perfusion system of the present embodiment preferably requires no operative and postoperative precautionary measures, which makes it possible to avoid or escape the possible complications which have been at issue in relation to the extracorporeal circulation and clamping of blood vessels, with the result that much more safe operation can be ensured while enjoying the merits resulting from the off-pump coronary artery bypass.

The invention has thus been shown and described with reference to specific embodiments, however, it should be understood that the invention is in no way limited to the details of the illustrated structures but changes and modifications may be made without departing from the scope of the appended claims.

What is claimed is:

1. A blood perfusion method comprising the steps of:
removing blood from an arterial vessel during a diastolic phase of a cardiac cycle;
pumping the removed blood with a syringe pump;
injecting the removed blood during a phase of the cardiac cycle other than a diastolic phase to a portion of a coronary artery with a perfusion device; and
controlling the pump to pump the blood at a selected speed, and in pulses having a predetermined amount of blood, the selected speed being based on an amount of blood injected by the perfusion device and a compliance of the perfusion device.

2. The blood perfusion method of claim 1, wherein the step of injecting the removed blood comprises using a catheter and a perfusion tube, the catheter sized to fit into the arterial vessel, and having a radially enlarged portion in fluid-tight contact with an inner wall of the arterial vessel, an identification color, and a reinforcing member preventing penetration thereof by a suture needle, the perfusion tube having a length, a thickness, and a flexibility greater than a length, a thickness, and a flexibility of the catheter, the flexibility of the perfusion tube being selected to permit blood flow in the catheter to be substantially similar to a physiologic blood flow.

3. The blood perfusion method of claim 1, further comprising the steps of:
controlling the syringe pump to pump the blood at a selected cycle, and selected volume, said selected speed, cycle, and volume determined by heart beat information received from an external monitoring device.

4. The blood perfusion method of claim 1, further comprising the steps of:
controlling the syringe pump to pump the blood at a selected cycle, and selected volume, said selected speed, cycle, and volume determined based on a predetermined value at an extreme bradycardia or a cardiac arrest.

* * * * *